(12) United States Patent
Ledig

(10) Patent No.: US 6,495,375 B2
(45) Date of Patent: Dec. 17, 2002

(54) PROCESS FOR COLLECTING FOR SUBSEQUENT ANALYSIS A VOLATILE COMPOSITION OF MATTER RELEASABLY BONDED TO A PLIABLE POROUS ROTATING SUBSTRATE

(75) Inventor: Walter O. Ledig, Matawan, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 96 days.

(21) Appl. No.: 09/761,365

(22) Filed: Jan. 16, 2001

(65) Prior Publication Data

US 2001/0016357 A1 Aug. 23, 2001

Related U.S. Application Data

(63) Continuation-in-part of application No. 09/336,055, filed on Jun. 18, 1999.

(51) Int. Cl.⁷ .................................................. G01N 1/22
(52) U.S. Cl. ....................... 436/181; 436/174; 436/176; 436/178; 73/23.34; 73/23.41; 73/23.42; 73/863.23
(58) Field of Search ................................. 436/181, 174, 436/176, 178; 73/232, 23.41, 23.42, 23.34, 863.23, 865.7, 866, 863.02

(56) References Cited

U.S. PATENT DOCUMENTS

| | | | |
|---|---|---|---|
| 4,462,880 A | * 7/1984 | Hill et al. ............... | 204/157.93 |
| 5,263,359 A | 11/1993 | Mookherjee et al. | |
| 5,305,493 A | * 4/1994 | Prenn ........................... | 15/304 |
| 5,891,729 A | 4/1999 | Behan et al. | |
| 5,891,835 A | 4/1999 | Vlasblom | |
| 6,050,129 A | 4/2000 | Shefer | |
| 6,106,786 A | 8/2000 | Akahoshi | |

OTHER PUBLICATIONS

Elmore, et al, *J. Agric. Food Chem.*, 1997, vol. 45, pp. 2638–2641 (title: "Comparison of Dynamic Headspace Concentration on Tenax with Solid Phase Microextraction for the Analysis of Aroma Volatiles").

* cited by examiner

*Primary Examiner*—Jill Warden
*Assistant Examiner*—Yelena Gakh
(74) *Attorney, Agent, or Firm*—Arthur L. Liberman

(57) ABSTRACT

Described is apparatus and a process for collection for subsequent analysis a volatile composition such as a perfume composition located on the surface and/or in the interstices of a planar pliable porous substrate such as a towel section. A planar surface of the substrate which contains the volatile composition is initially juxtaposed adjacent a solid wall (e.g., glass frit) porous to a nonreactive carrier gas such as air, nitrogen or carbon dioxide, and fully and tightly covers the porous section of the wall. The carrier gas is passed through the porous section of the wall and then through the pliable porous substrate section which is adjacent to the wall; after which the carrier gas contains each component of the volatile composition. The composition-carrier gas mixture is then passed through a trapping substance (e.g., TENAX®) which entraps the molecules of each component of the volatile composition. The thus-collected volatile composition may subsequently be analyzed (e.g., using GLC and NMR techniques) after removing the trapping substance containing the entrapped components from the apparatus.

In a second embodiment of the invention the planar porous substrate is attached to a rigid frame and the frame is rotated and the movement of the fragrance from the substrate is measured.

14 Claims, 14 Drawing Sheets

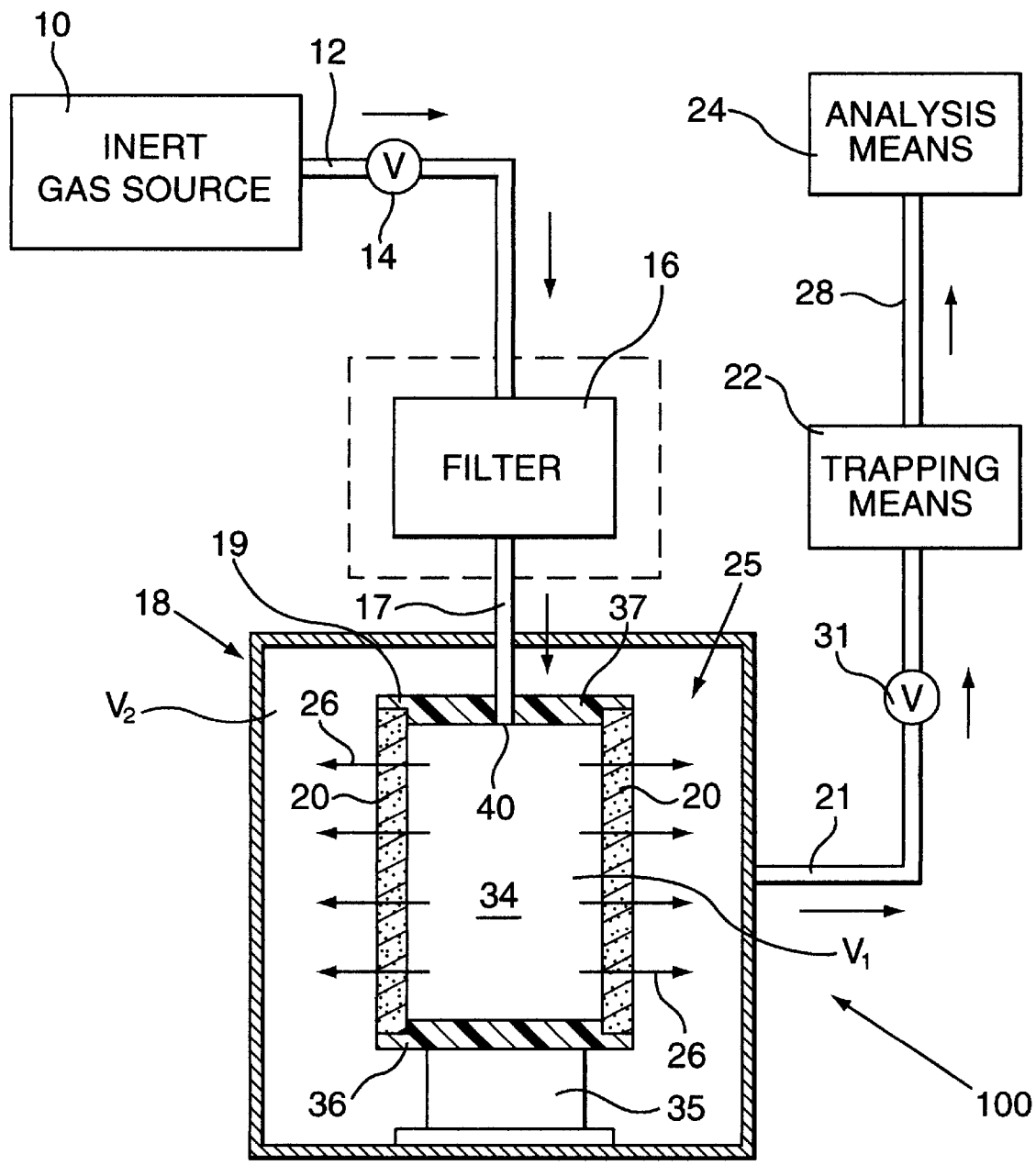
FIG. 1-A

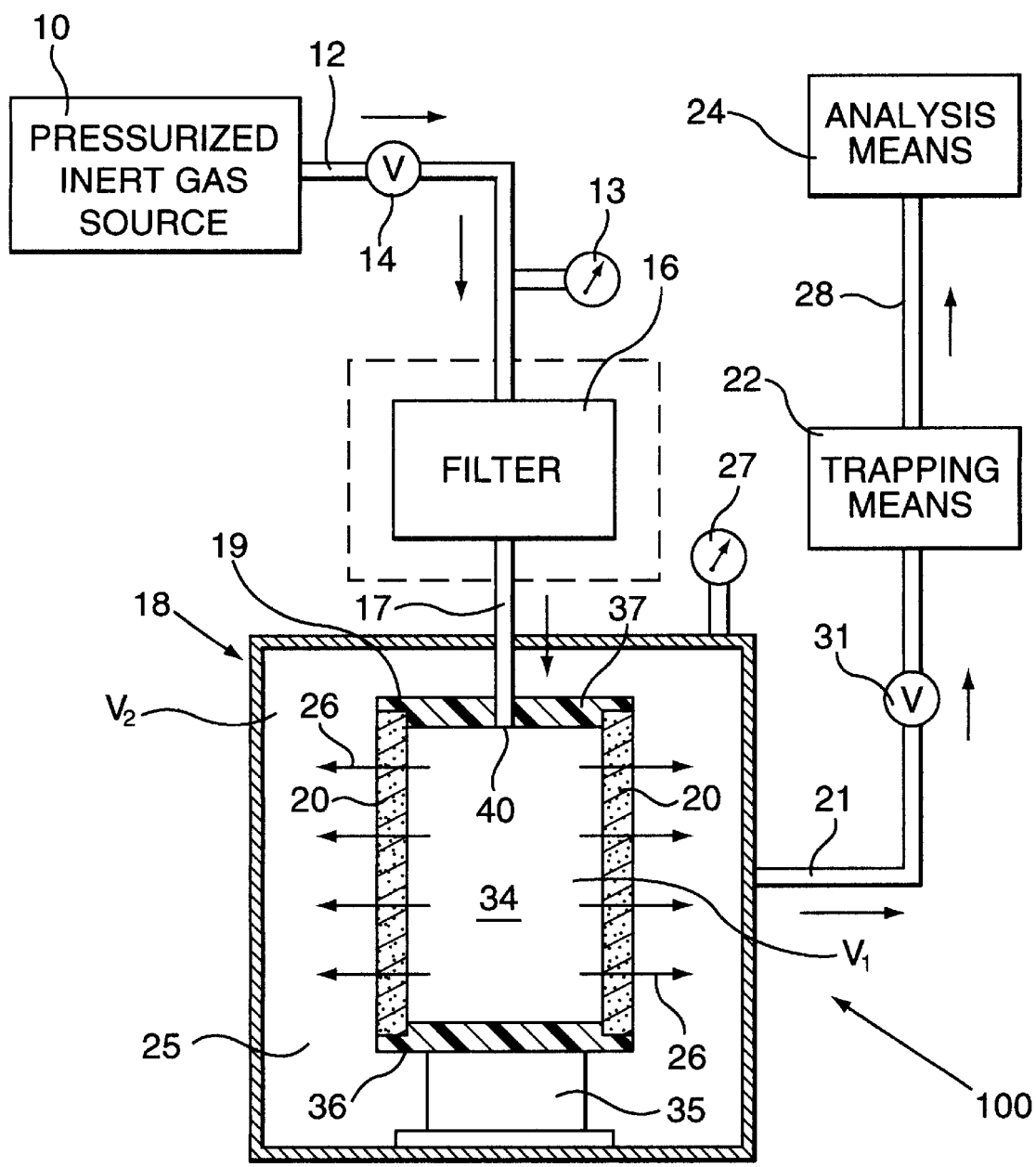
FIG. 1-B

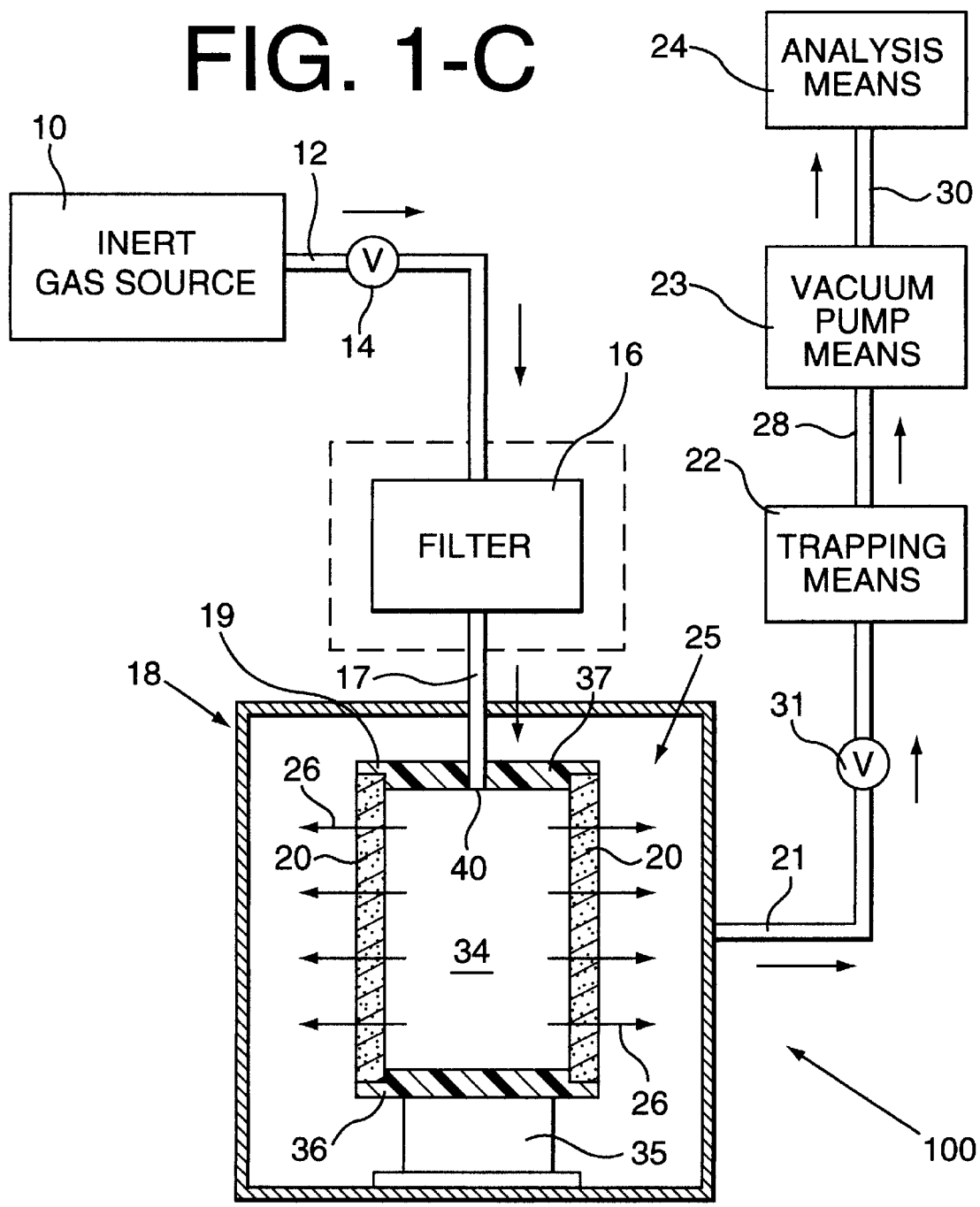
FIG. 1-C

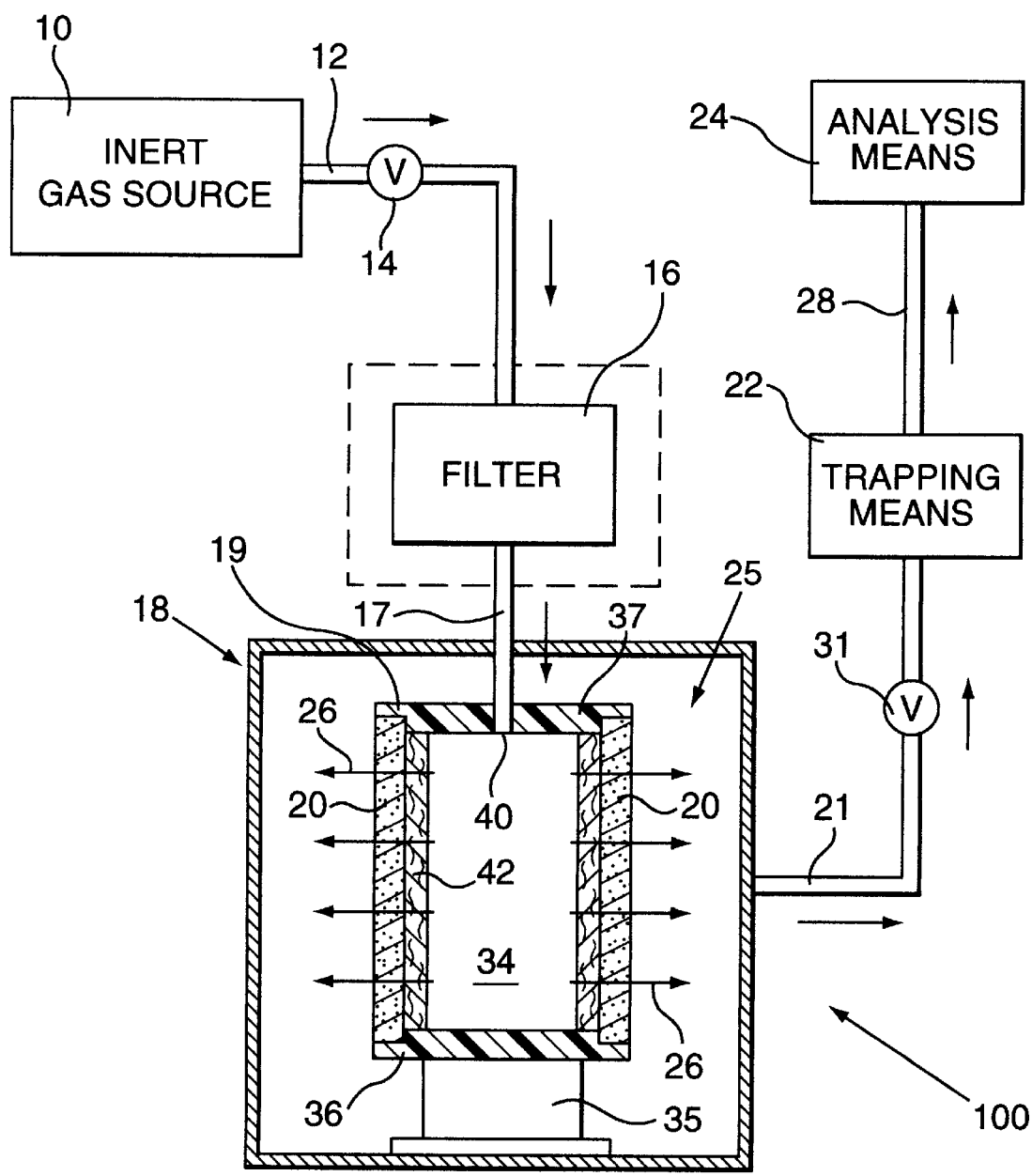
FIG. 1-D

FIG.1-E
PRIOR ART
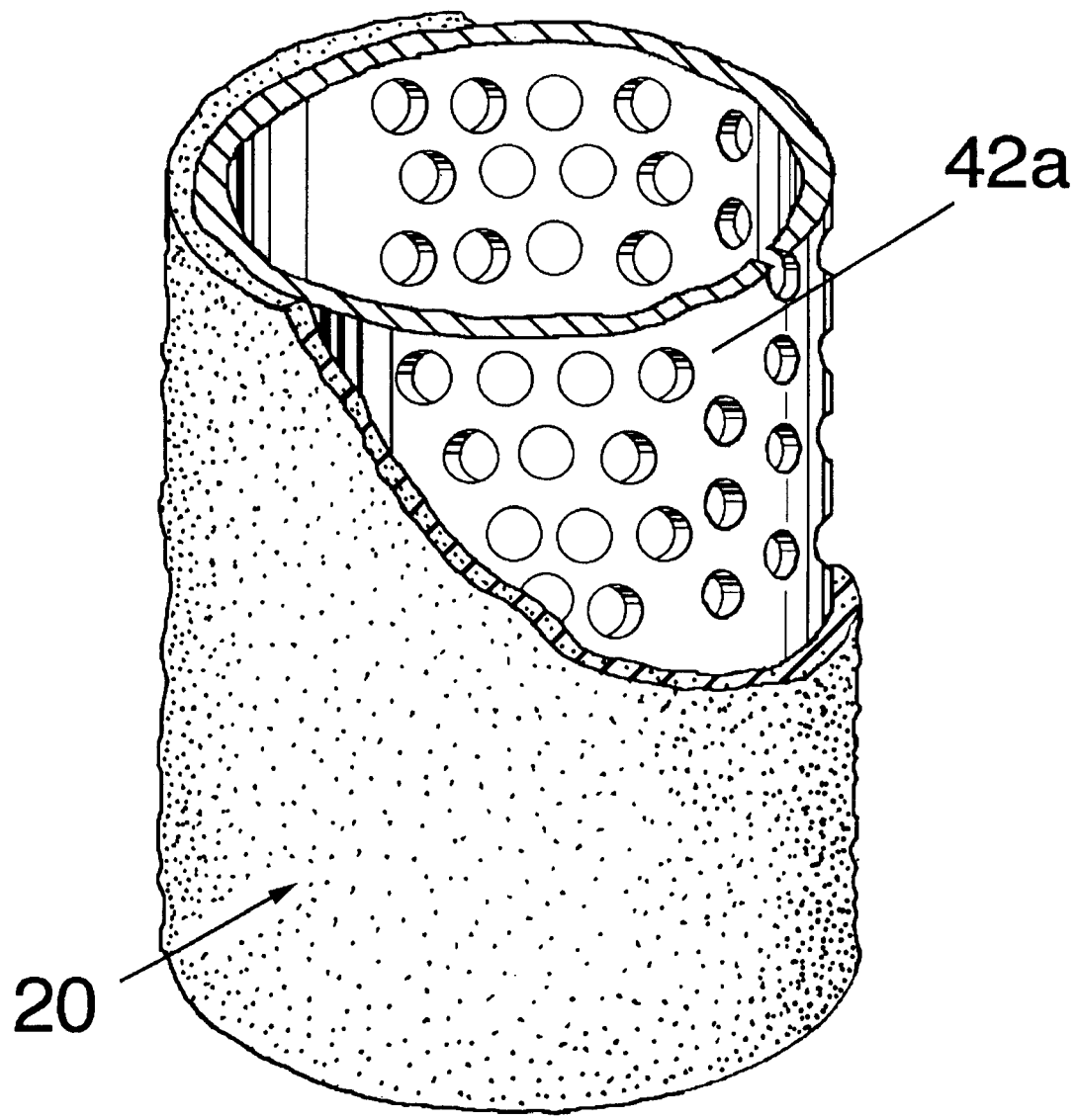

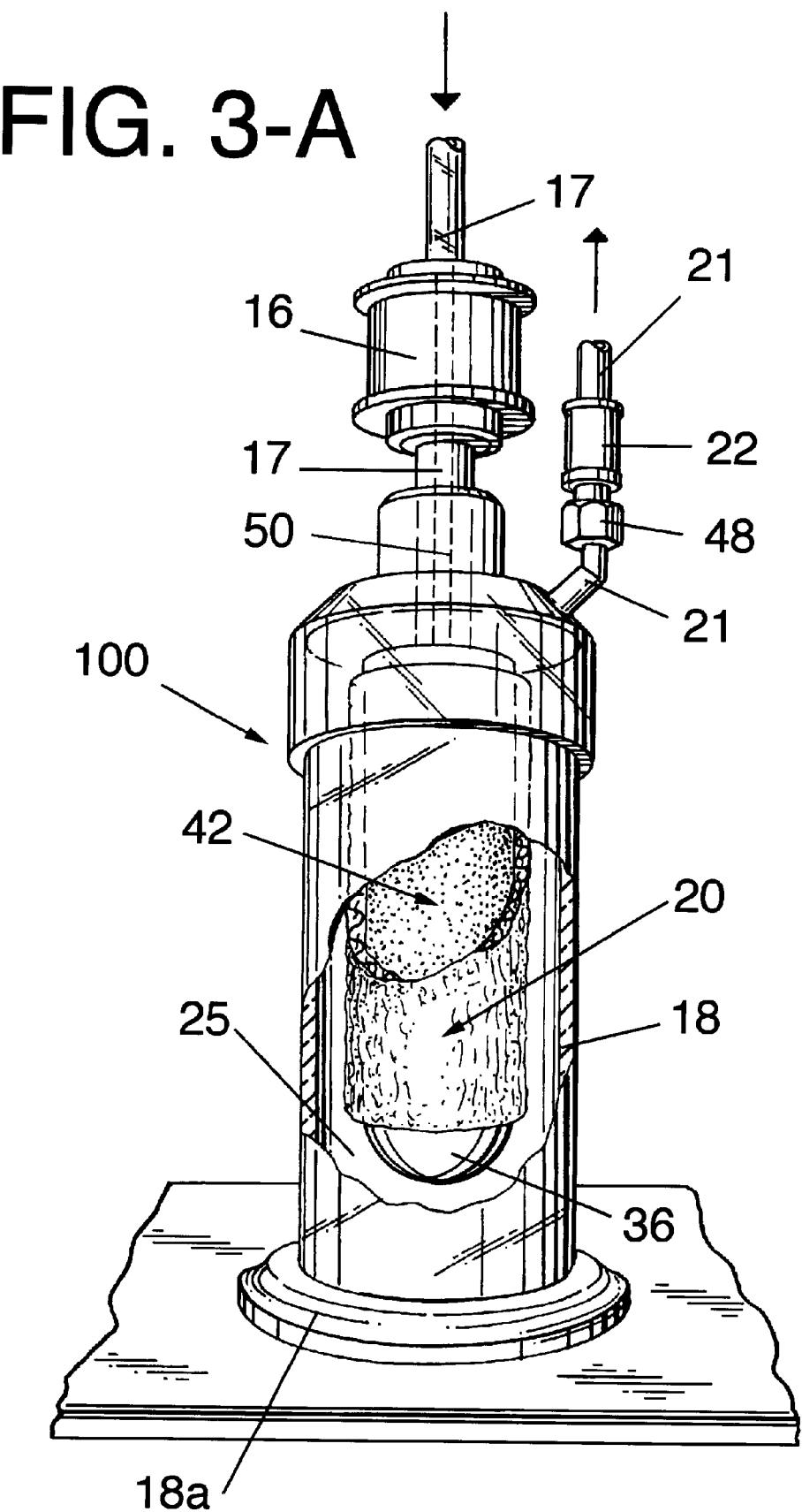

FIG. 3-B
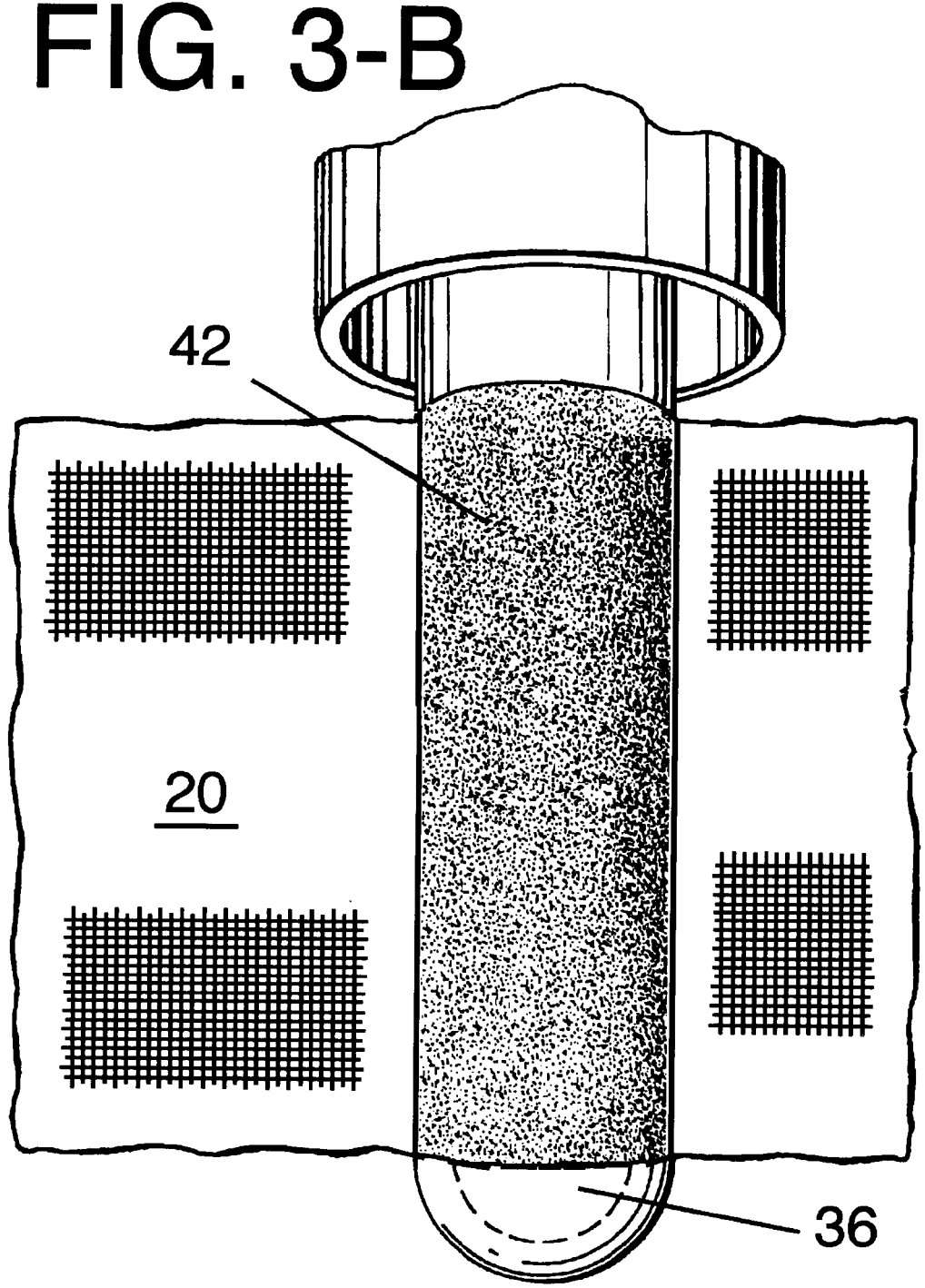

FIG. 3-C
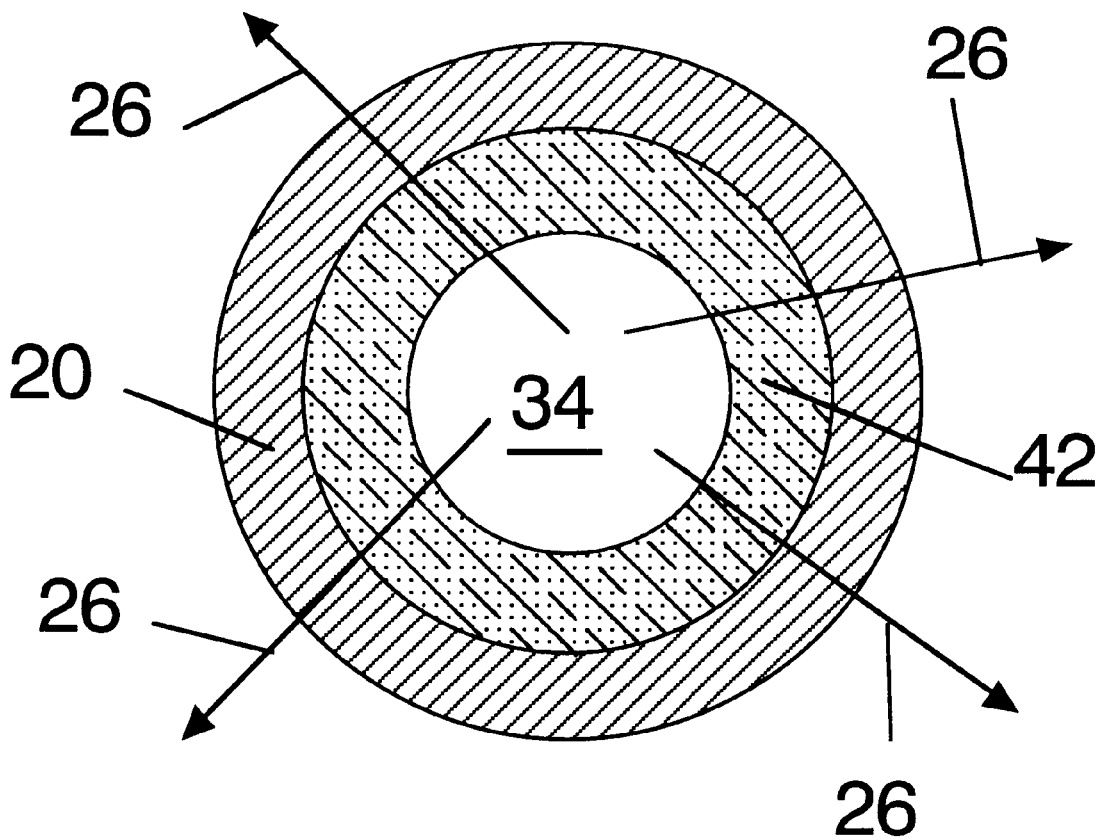

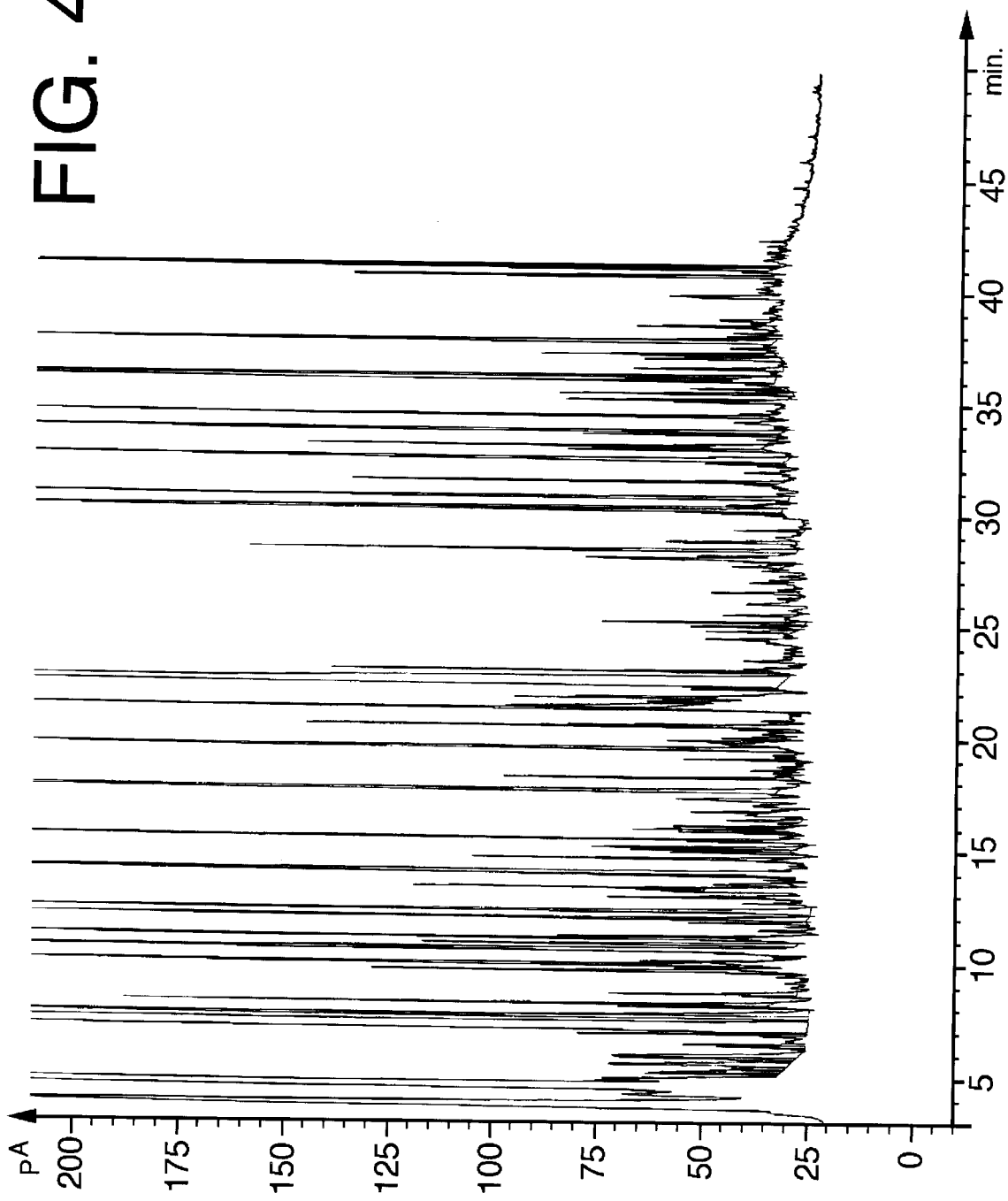

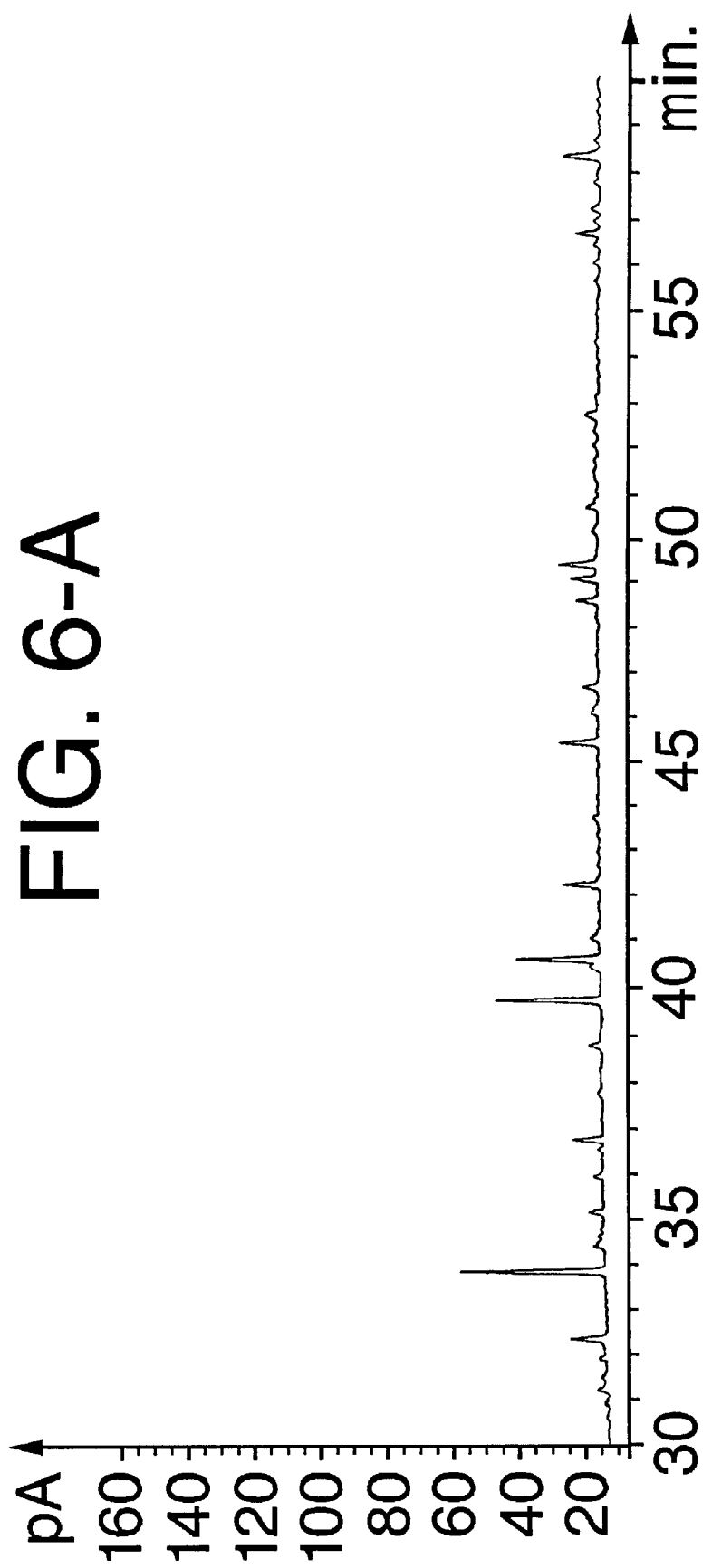
FIG. 6-A

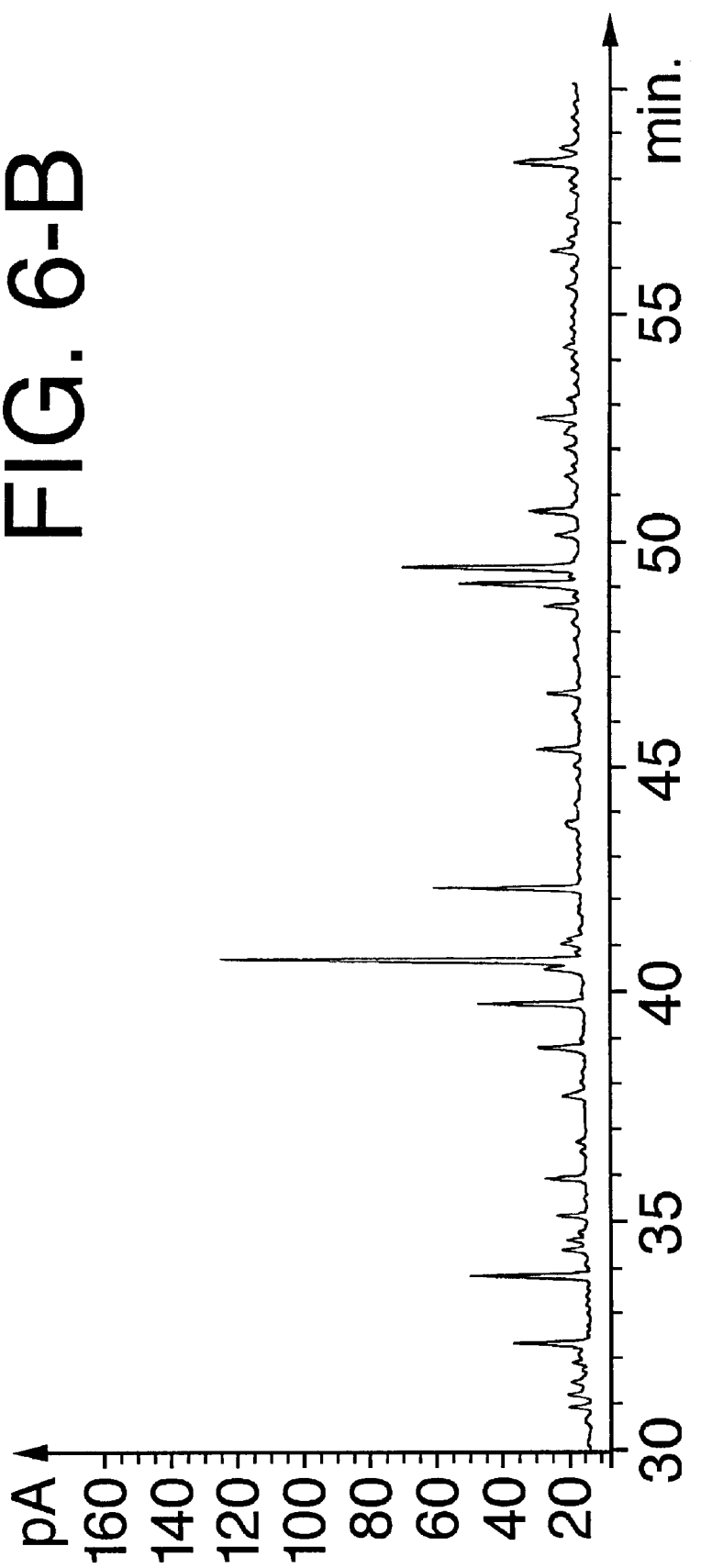

PROCESS FOR COLLECTING FOR SUBSEQUENT ANALYSIS A VOLATILE COMPOSITION OF MATTER RELEASABLY BONDED TO A PLIABLE POROUS ROTATING SUBSTRATE

RELATED APPLICATION

This application is a continuation-in-part of my application filed on Jun. 18, 1999, U.S. Ser. No. 09/336,055, the contents of which are hereby incorporated by reference as if set forth in its entirety.

BACKGROUND OF THE INVENTION

My invention covers apparatus for collecting (for purposes of subsequent analysis) a volatile composition of matter which is releasably bonded to a pliable porous substrate such as a towel, as well as a process for using such apparatus.

The properties of a pliable substrate (including physical, chemical and microbiological properties) affect the behavior of the substrate with respect to chemicals, particularly volatile chemicals, either naturally present in or on the substrate in a substance applied thereto and so affect the chemicals present in a headspace above the substrate. Conversely, the chemicals entrapped in the interstices of a porous substrate or on the surface of the porous substrate have an effect upon the properties of the substrate, for example, if the substrate is a towel and the towel contains a fragrance, the concentration of that fragrance and the nature of the fragrance in the particular substrate will affect the ultimate aroma in the headspace above the substrate after the substrate is utilized, washed and dried.

Considerably complicated techniques exist in the prior art for collection for purposes of subsequent analysis of volatile materials contained within a substrate. U.S. Pat. No. 5,891,729 discloses a method of characterizing a substrate which comprises applying a test formulation to said substrate, subsequently collecting volatile chemicals in a headspace above the substrate, determining a profile of the volatile chemicals so emanated and using said profile to characterize the substrate. Specific examples of substrates in U.S. Pat. No. 5,891,729 are skin, wood, hair, clothing, carpets, plastics, surfaces, ceramic tiles, wool, fabric or perfumed products.

Noting the complexity of the methods and techniques of U.S. Pat. No. 5,891,729, it is apparent that a need exists for a more standardized and simplified technique for collection (for purposes of subsequent analysis) of a volatile composition of matter releasably bonded to a pliable porous substrate such as a towel.

Thus, for example, U.S. Pat. No. 5,891,835 issued on Apr. 6, 1999 discloses a cleaner impregnated towel comprising a flexible porous substrate and impregnated into the substrate a cleaner formulation comprising d-limonene, dibasic acid ester, N-methyl-2-pyrrolidone, secondary alcohol ethoxylate, sodium lauryl sulfate, polysorbate 80, a salt of a coconut oil, fatty acid ester of isethionic acid, glycerine, ethyl alcohol, an antimicrobial preservative and, optionally, water. Although the composition impregnated into the substrate is known initially, after the substrate is utilized, there is no teaching of the method for collecting (for purposes of subsequent analysis) the components impregnated into the substrate after initial use or after repeated use of the substrate, nor is there any teaching in U.S. Pat. No. 5,891,835 or U.S. Pat. No. 5,891,729 of apparatus or processes for a simplified technique for collecting (for purposes of subsequent analysis) the contents of such substrate.

SUMMARY OF THE INVENTION

My invention is directed to a process for the utilization of apparatus which will effect collection (for purposes of subsequent analysis) of compounds in the headspace over dry cloth as well as moist cloth and other substrates. The compounds are releasably bonded to the surface and/or in the interstices of the porous substrate.

More specifically, my invention is directed to a process for collection (for purposes of analysis) of a volatile composition such as a perfumery composition located on the surface and/or in the interstices of a planar pliable porous substrate such as a towel section.

In practicing my invention, a planar surface of the substrate which contains the volatile composition is initially juxtaposed adjacent a solid wall (e.g., glass frit) porous to a nonreactive carrier gas such as air, nitrogen or carbon dioxide and fully and tightly covers the porous section of the wall. The carrier gas is passed through the porous section of the wall and then through the pliable porous substrate section which is adjacent the wall, after which the carrier gas will contain each component of the volatile composition. The composition-carrier gas mixture is then passed through a trapping substance (e.g.,TENAX® (Registered Trademark of BUCHEM, B. V. of Apeldoorn, Netherlands), a polyphenylene oxide having a CAS Registration Number,2438-68-9) which entraps the molecules of each component of the volatile composition. The volatile composition can then be analyzed (e.g., using GLC, NMR and mass spectral techniques) after removing the trapping substance containing the entrapped molecules from the apparatus.

Thus, my invention is directed to a process for using apparatus for collecting (for purposes of subsequent analysis) components of a volatile substance such as a perfumery material releasably bonded to a substantially planar pliable porous substrate having an inner surface and an outer surface. The substrate is porous to the passage of a carrier gas therethrough in a direction substantially perpendicular to the inner and outer surfaces of the planar pliable porous substrate. The apparatus consists essentially of:

(a) hollow enclosure means (which can be cylindrically shaped or elliptical-cylindrically shaped) having:
  i. hollow outer enclosure means circumventing a first void space and consisting essentially of a base supporting a substantially cylindrical gas impermeable wall having exit port means therethrough;
  ii. entirely surrounded by said hollow outer enclosure means, substantially cylindrically-shaped inner enclosure means situated within said first void space and circumventing a second void space, and having two spaced-apart oppositely-situated end sections and a central section juxtaposed to and communicating with each of said oppositely-situated end sections, said central section being substantially parallel to the wall of said outer enclosure means, said central section having an outer surface and an inner surface, and said central section consisting of a cylindrically-shaped gas-permeable hollow frit structure for both (A) supporting the pliable porous substrate whereby, when in use, said porous substrate fully covers said laminar gas-permeable central section in an all-encompassing manner and (B) enabling carrier gas to flow from within said inner enclosure means second void space to the void space located between the outer enclosure means and the inner enclosure means, in a direction substantially perpendicular to and through said porous substrate, each of the two end sections being impervious to the flow of gas therethrough and one of said end sections having an entry port means communicating from without said hollow enclosure means to the second void space within said inner enclosure means;

(b) analyte collection means located downstream from said hollow enclosure means and communicating with the exit port means thereof, consisting essentially of tube trapping means whereby analyte mixture components emitted from said pliable porous substrate during gas flow therethrough are entrapped in said tube trapping means;

(c) upstream from said hollow enclosure means or downstream from said analyte collection means, inert gas flow effecting means for effecting the flow of inert gas sequentially (I) through said entry port means; (II) through the porous pliable substrate means located on said hollow frit structure; (III) through said exit port means; and (IV) through said analyte collection means.

More specifically, my invention is directed to a process for collecting (for purposes of subsequent analysis) a volatile substance (such as a fragrance composition or an insect-repelling composition) releasably bonded to a substantially planar pliable porous substrate (for example, a cloth or a towel fabricated from cotton or polyester) having an inner surface and an outer surface comprising the step of:

(a) providing the apparatus as set forth, supra;

(b) providing said porous substrate;

(c) wrapping in an all-encompassing manner said porous substrate around said central section of said inner enclosure means of said apparatus whereby the inner surface of said porous substrate is removably adhered to and intimately adjacent to the entirety of the outer surface of the hollow frit structure of the inner enclosure means; and (d) effecting the flow of carrier gas sequentially (I) from a location upstream from the entry port means; (II) into the inner enclosure means through said entry port means; (III) through said hollow frit structure; (IV) through said porous substrate means in a direction substantially perpendicular thereto in a substantially evenly distributed manner across the inner and outer surface thereof; (V) into and through the void space between the inner enclosure means and the outer enclosure means; (VI) through said exit port means of said hollow outer enclosure means; and (VII) into and through said analyte collection means, whereby components of the analyte composition emitted from said porous substrate are trapped in said tube trapping means.

Another embodiment of the present invention provides for the rotation of framing retaining means to which is attached the pliable porous substrate, for example a towel, thereby releasing a volatile composition of matter from the substrate. More specifically, the present invention provides for methods for using apparatus designed for the purpose of carrying out this embodiment.

Thus, the invention employs apparatus for collecting (for purposes of subsequent analysis) a volatile substance releasably bonded to a substantially planar pliable porous substrate having an inner surface and an outer surface, said substrate being porous to the passage of a carrier gas consisting essentially of:

(a) vertically-positioned rotational shaft means having an upper end section, a middle section, a lower end section, and a vertically-disposed shaft means axis;

(b) vertically-positioned framing retaining means connected to said lower end section of said rotational shaft means;

(c) hollow substantially air-tight enclosure means surrounding a void space, supported on a horizontally-disposed supporting means, and having a horizontally-disposed lid, a vertically-positioned cylindrical wall circumventing and extending upwardly from said horizontally-disposed supporting means and downwardly from the circumference of said horizontally-disposed lid, a vertical enclosure means axis, carrier gas exit port means therethrough, carrier gas first entry port means therethrough, gas-impermeable second entry port means therethrough located at the intersection of said vertical enclosure means axis and said lid for sealably holding in place said rotational shaft means at its middle section with the vertically-disposed shaft means axis of said rotational shaft means being coincident with said vertical enclosure means axis and sealably extending through said second entry port means into said void space and with said vertically-positioned framing retaining means being supported by and attached to said rotational shaft means located at the lower end section of said rotational shaft means, for retaining said pliable porous substrate;

(d) attachment means for attaching said pliable porous substrate to said framing retaining means;

(e) rotational motor means attached to the upper end section of said rotational shaft means for causing said rotational shaft means to rotate about said vertically-disposed shaft means axis when said apparatus is in operation;

(f) analyte collection means located downstream from said hollow enclosure means and communicating with said exit port means thereof, consisting essentially of tube trapping means whereby analyte mixture components emitted from said pliable porous substrate during gas flow therethrough are entrapped in said tube trapping means; and (g) upstream from said hollow enclosure means or downstream from said analyte collection means, gas flow effecting means for effecting the flow of gas sequentially (I) from a location upstream from said first entry port means; (II) through said first entry port means; (III) into said hollow enclosure means in a direction substantially perpendicular to the plane of said porous substrate located on and attached to said framing retaining means; (IV) onto the inner surface of said porous substrate; (V) through said porous substrate, exiting from said outer surface thereof; (VI) through said exit port means of said hollow enclosure means and (VII) into and through said analyte collection means.

The method of my invention consists essentially of the use of the apparatus described above as follows:

A process for carrying out collection of analyte, for the purpose of effecting qualitative and quantitative analysis of a volatile analyte composition releasably bonded to a substantially pliable porous substrate having an inner vertically-positioned surface and an outer vertically-positioned surface, said substrate being porous to the passage of a carrier gas and being fixedly retained by a rigid framing retaining means, as a vertically positioned substantially planar lamina, consisting essentially of the steps of:

(a) providing the apparatus set forth hereinabove;

(b) providing said porous substrate and attaching said porous substrate via said attachment means to said framing retaining means;

(c) engaging said rotational motor means;

(d) simultaneously with the engagement of said rotational motor means, upstream from said hollow enclosure means or downstream from said analyte collection means effecting the flow of carrier gas sequentially (I) from a location upstream from said first entry port means; (II) through said first entry port means; (III) into said hollow enclosure means in a direction substantially perpendicular to the plane of said porous substrate located on and attached to said framing retaining means; (IV) onto the inner surface of said porous substrate; (V) through said porous substrate, exiting from said outer surface thereof; (VI) through said exit port means of said hollow enclosure means and (VII) into and through said analyte collection means whereby volatile substance components emitted from said porous substrate are trapped in said analyte collection means.

DETAILED DESCRIPTION OF THE INVENTION

Preferably, the hollow enclosure means of the above-described apparatus contains two concentric cylindrical enclosures, with the outer cylindrical enclosure being impervious to gas except for an exit port and with the inner enclosure means having an entry port and having a centrally located solid porous surface (e.g,., glass frit, or solid microporous polymer).

Preferably, after the pliable porous substrate is in place on the inner enclosure, carrier gas is forced through the inner enclosure past the porous substrate into the outer enclosure and then out of the outer enclosure into the analytical means which preferably contains a trapping material. The carrier gas, such as nitrogen, air or carbon dioxide, is inert and nonreactive with the porous substrate or with the volatile substance releasably bonded to the porous substrate. The carrier gas can either be forced through from a pressurized device upstream from the hollow enclosure means (e.g., a pressurized carbon dioxide cylinder), or the carrier gas can be pulled through using means downstream from the analytical apparatus means such as a vacuum pump.

Whether the inert gas flow effecting means is upstream from the remainder of the apparatus or downstream from the remainder of the apparatus, it is preferable to have a gas filter in place in the apparatus of my invention, upstream from the hollow enclosure means so that the inert gas is free of any contaminants which would interfere with the analysis of the composition releasably bonded to the substantially planar pliable porous substrate (e.g., towel section).

Preferably, the hollow outer enclosure means of the hollow enclosure means part of the apparatus of my invention is cylindrical and has a height dimension of from about 4 cm up to about 20 cm and a diameter dimension of from about 4 cm up to about 12 cm. Preferably, the inner enclosure means of the hollow enclosure means part of the apparatus of my invention is cylindrical and has a height dimension between from about 50% up to about 85% of the height dimension of the hollow outer enclosure means and a diameter dimension of from about 40% up to about 70% of the diameter dimension of the hollow outer enclosure means.

The support means part of the inner enclosure means (that is, the central section of the inner enclosure means) is preferably cylindrical or substantially cylindrical in shape and as stated, supra, is preferably glass frit or microporous polymer. However, other suitable support means are useful in the practice of my invention, for example, the material which is marketed as cylindrical filter screens by the B. C. McDonald & Company of St. Louis, Mo. 63132 under the description of "Ronningen-Petter Woven Wire Screen"; or Ronningen-Petter Woven Synthetic Screen (illustrated in FIG. 1E which is described in the Brief Description of the Drawings and in the Detailed Description of the Drawings sections, infra); or the Ronningen-Petter Perforated Screen. The Ronningen-Petter Screens are manufactured by the Dover Corporation/Ronningen-Petter Division, P.O. Box 188, Portage, Mich. 49081. The Ronningen-Petter Cylindrical Screens useful as support means in the practice of our invention are specifically described in literature published by Ronningen-Petter entitled "*How to Select Filter Screens for the Removal of Trace Contaminants in a Closed Liquid System.*"

Other support means useful in fabrication of the central section of the inner enclosure means of the apparatus of my invention are described in U.S. Pat. No. 5,762,797 issued on Jun. 9, 1998 entitled "ANTIMICROBIAL FILTER CARTRIDGE," the specification for which is incorporated by reference herein, and U.S. Pat. No. 5,868,933 issued on Feb. 9, 1999 entitled "ANTIMICROBIAL FILTER CARTRIDGE", the specification for which is incorporated by reference herein.

With respect to the analyte collection means located downstream from the hollow enclosure means and communicating with the exit port means of the hollow outer enclosure means, the analyte collection part of the apparatus of my invention as stated, supra, consists essentially of tube trapping means whereby volatile substance components emitted from the pliable porous substrate during gas flow therethrough are entrapped in the tube trapping means. The tube trapping means preferably consists of a tube having a length in the range of from about 2 cm up to about 4 cm and a diameter of from about 0.1 cm up to about 0.4 cm. Thus, various trapping materials are useful in the practice of my invention. As stated, supra, TENAX® is a preferable material. Various forms of TENAX® are useful, for example, TENAX®-GC. TENAX® is a registered trademark of ENKA, N.V. of the Kingdom of the Netherlands (CAS Registration No. 2438-68-9). Other forms of TENAX® and methods of production of such forms of TENAX® are described in the following U.S. Letters Patents, the disclosures of which are incorporated by reference herein:

U.S. Pat. No. 3,400,100 issued on Sep. 30, 1968 ("PROCESS FOR THE PREPARATION OF POLYPHENYLENE ETHERS");

U.S. Pat. No. 3,644,227 issued on Feb. 22, 1972 ("SEPARATION OF POLY (2,6-DIMETHYL-1,4-PHENYLENEOXIDE)") FROM ITS BLENDS WITH OTHER POLYMERS);

U.S. Pat. No. 3,703,564 issued on Nov. 21, 1972 (BIS-POLYPHENYLENEOXIDE]ESTER BLOCK COPOLYMERS");

U.S. Pat. No. 4,431,779 issued on Feb. 14, 1984 (POLYETHERAMIDE-POLYPHENYLENE ETHER BLENDS"); and U.S. Pat. No. 4,801,645 issued on Jan. 31, 1989 ("THERMOPLASTIC RESIN COMPOSITION").

TENAX®-GC is actually a polyphenyleneoxide defined according to the structure:

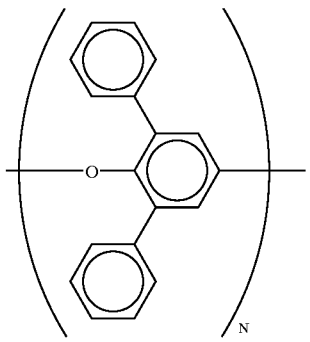

wherein N is an integer of from about 100 up to about 150.

Other trapping materials useful in the practice of my invention are as follows:

Activated Carbon marketed by Aldrich Chemical Company of 1001 West Saint Paul Avenue, Milwaukee, Wis. 53233 (Catalog Nos. 16, 155-1; 29, 259-1; 24, 223-3; 24, 224-1; and 24, 227-6);

Activated Alumina marketed by Sigma Chemical Company of St. Louis, Mo. (Catalog Nos. A8753; A8878; A9003; A1522; and A2272);

Silica Gels marketed by Sigma Chemical Company (for example, Catalog Nos. S4004; S6628; and H8506); and CHROMOSORB® (registered trademark of the Johns-Manville Company of Manville, N.J.), such as CHROMOSORB® LC-2; CHROMOSOPB® LC-3; AND CHROMOSORB® LC-7, marketed by Sigma Chemical Company under Catalog Nos. C 0641; C 0766; C 5517 and C 6269.

The analyte collection means useful in the practice of my invention may contain, in place of the TENAX® trapping substance, solid phase microextraction materials ("SPME" materials) such as those described in *Bulletin* 869 published by SUPELCO, INC., Supelco Park, Bellefonte, Pa. 16823-0048. An SPME example useful in the practice of my invention is 100 μm polydimethylsiloxane fiber, Catalog No. 5-7300 of Supelco, Inc. The Supelco, Inc. *Bulletin* 869 is incorporated by reference herein. An additional description of the SPME (solid phase microextraction) technique useful in conjunction with the practice of my invention is the paper, Elmore, et al, *J. Agric. Food Chem.*, 1997, Volume 45, pages 2638–2641, entitled "Comparison of Dynamic Headspace Concentration on Tenax [TENAX®] with Solid Phase Microextraction for the Analysis of Aroma Volatiles," incorporated by reference herein.

As stated, supra, the means for effecting the flow of inert gas sequentially (i) through the entry port means of the inner enclosure means; (ii) and through the porous pliable substrate means located on the support means of the apparatus of my invention can be located downstream from the analytical apparatus means. If that is the case, the inert gas flow effecting means is a negative pressure pump means, preferably a vacuum pump of the "low flow" variety, for example, "Low Flow" pumps marketed by the Ametek Company of Largo, Fla. 34643 (the "Ametek Constant flow Sampler").

The flow rate of inert carrier gas past the porous pliable substrate is preferably at a rate in the range of from about 20 ml per minute up to about 200 ml per minute of carrier gas, e.g., nitrogen, air or carbon dioxide.

At the indicated rates of carrier gas flow, a range of molar rates of release of volatile composition will occur from the porous substrate, e.g., towel section, in accordance with the following algorithm:

$$\Delta n = n_1 \left[ \frac{V_1}{V_2} e^{-\frac{2C_V}{zR} \left[ \frac{T_2 - T_1}{T_2 + T_1} \right]} - 1 \right]$$

wherein $n_1$ is the carrier gas flow rate in gram moles per hour;

$\Delta n$ is the molar flow rate (in gram moles per hour) of release of volatile composition from the pliable porous substrate;

$V_1$ is the volume of the inner enclosure;

$T_1$ is the temperature of the void space of the inner enclosure in °K (degrees Kelvin);

$V_2$ is the volume between the porous pliable substrate and the outer enclosure;

$T_2$ is the temperature of the carrier gas and volatile composition released from the pliable porous substrate (that is, the temperature of volume $V_2$) in °K;

R is the gas constant $$\left[ 0.08206 \frac{\text{liter} - \text{atm}}{\text{gm mole} - °\text{K.}} \right];$$

z is the compressibility factor of the carrier gas; and $C_v$ is the heat capacity of the carrier gas defined as $$\left( \frac{\partial E}{\partial T} \right)_V,$$

wherein E is the internal energy of the carrier gas during flow through the apparatus of my invention.

In another embodiment of the present invention, the pliable porous substrate is put into motion, preferably rotated, most preferably rotated at a controlled rate to simulate the ability of a fragrance to be released from the substrate when the substrate is moved. For example, this movement is intended to simulate the release of a fragrance from a sheet when the sheet is being placed upon a bed.

When the substrate is rotated it is desirable to provide a gentle, but thorough movement of the substrate. The movement can be done in various directions, such as a back and forth motion, an elliptical motion or most preferably in a circular motion. The circular motion is most preferred in that the rotation of the substrate on a rotating shaft is easily accomplished as well as providing a seal between the rotating shaft and enclosure means. The enclosure means could be enlarged such that all equipment is enclosed within the enclosure means; however, that makes collection (for purposes of subsequent qualitative and quantitative analysis) of the volatile compounds that are removed from the substrate more difficult.

Preferably, the rotating shaft is controlled via a motor means such as an electric motor, preferably by a variable control source. The rotation of the shaft should be from about 10 to about 150 revolutions per minute, typically from about 30 to about 120 and preferably from 50 to about 90 revolutions per minute. In a highly preferred embodiment, the rotation of the substrate should be about 82 revolutions per minute. This rpm is sufficient to simulate the movement of the substrate in routine motion without being unduly harsh, thereby removing too much of the fragrance, or too gently which might not release sufficient fragrance from the substrate.

The carrier gas, preferably an inert gas, is provided at a rate of from 0.1 to about 1.0 liter/minute, typically from about 0.2 to about 0.8 and preferably from about 0.3 to about 0.7 liter/minute. The most preferred flowrate is about 0.5 liter/minute.

The analysis of the headspace is carried out in the same manner as described hereinabove. The analysis means (not part of my invention) monitors the headspace of the enclosure means in a substantially continuous manner. The contents of the headspace is then carried onto the trapping materials and the analysis is conducted as described herein above.

BRIEF DESCRIPTION OF THE DRAWINGS

FIG. 1A is a schematic block flow diagram showing the operation of the apparatus of my invention and the process of my invention.

FIG. 1B is another schematic block flow diagram showing the operation of the apparatus of my invention as well as the process of my invention and showing the use of pressure measuring devices in conjunction with the apparatus of my invention; and, in addition, showing the use of inert gas flow effecting means for effecting the flow of inert gas through the apparatus of my invention, upstream from the hollow enclosure portion of the apparatus of my invention, specifically as a pressurized gas source (e.g., cylinder of pressurized air).

FIG. 1C is another schematic block flow diagram showing the operation of the apparatus of my invention and the process of my invention and also showing inert gas flow effecting means for effecting the flow of inert gas through the apparatus of my invention, which flow effecting means is in the form of vacuum pump means downstream from the analytical apparatus means.

FIG. 1D is another schematic block flow diagram showing the use of the apparatus of my invention when in actual operation analyzing a pliable porous substrate material containing material to be collected (for purposes of subsequent analysis) (e.g., a fragrance composition).

FIG. 1E is a cutaway perspective diagram of an example of a laminar gas-permeable section of the central section of the inner enclosure means of the apparatus of my invention ("Ronningen-Petter Woven Synthetic Screen" manufactured by the Ronningen-Petter Division of the Dover Corporation, P.O. Box 188, Portage, Mich. 49081).

FIG. 3A is a perspective view of a preferred embodiment of the apparatus of my invention, showing the outer enclosure means fabricated from ceramic quartz glass and showing the central part of the inner enclosure means fabricated from fritted glass.

FIG. 3B is a perspective view of a preferred embodiment of that part of the apparatus of my invention which is the inner enclosure means wherein the central section consists of a fritted glass laminar gas-permeable section and wherein the porous pliable planar substrate to be analyzed is a towel section about to be placed fully covering and adjacent to the fritted glass section of the inner enclosure means.

FIG. 3C is a top cutaway schematic view of the inner enclosure means of the apparatus of my invention having juxtaposed and adjacent thereto the porous pliable substrate to be analyzed for a volatile composition contained thereon or in the interstices thereof.

FIG. 4 is the GC-mass spectrum of a fragrance composition releasably bonded to a towel section, which composition was collected (for purposes of subsequent analysis) using the process of my invention according to the procedure of Example I, infra (conditions: 50 meter×320 $\mu$×0.52 $\mu$ bonded fused silica methyl silicone column programmed from 80–220° C. at 8° C. per minute).

FIGS. 6A and 6B are chromatograms of a fragrance, measured while the pliable substrate is stationary and retested while it is in motion.

DETAILED DESCRIPTION OF THE DRAWINGS

Figure 2:
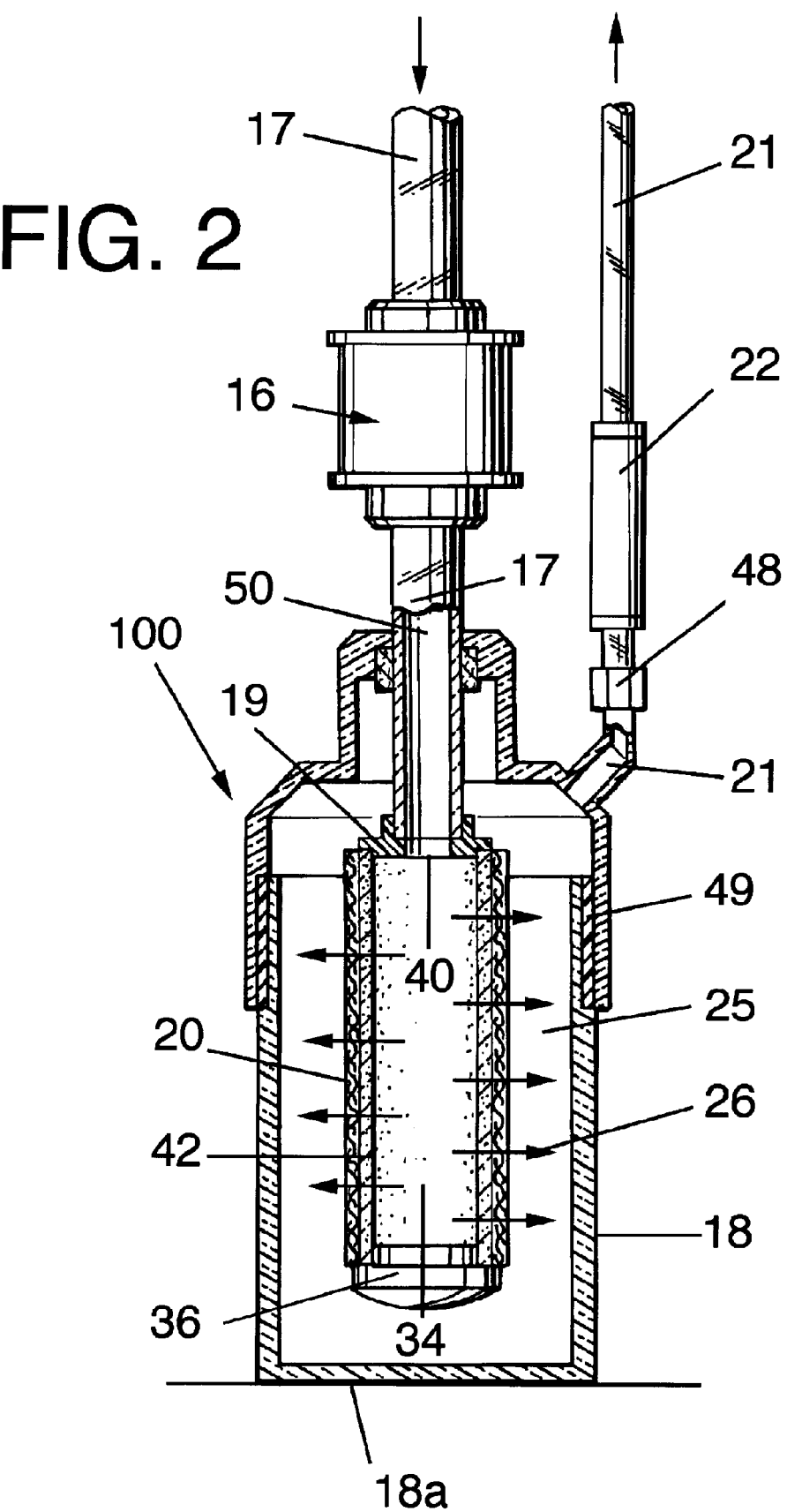
FIG. 2 is a detailed cutaway side elevation view of a preferred embodiment of the apparatus of my invention showing the employment of fritted glass as a laminar gas permeable section of the central section of the inner enclosure means of the apparatus of my invention.

Referring to FIGS. 1A, 1B, 1C and 1D, gas from gas source 10 is passed through line 12 past valve 14 through carrier gas filter 16 (optionally) through line 17 into the inner enclosure means 19, which is a support means for porous material 20. The carrier gas passes through entry port 40 into void 34. The inner enclosure means has top 37 and base 36. The inner enclosure means is supported via support 35 within the outer enclosure means 18. Carrier gas flows from void 34 into void 25 of the outer enclosure means (with the flow being shown by reference numeral 26). The carrier gas is then passed through line 21 past valve 31 into and through trapping means 22 wherein components of volatile material from the porous material at 20 are trapped. The trapping substance containing the trapped components may then conveyed via route 28 to analysis means 24 (e.g., NMR, IR and mass spectral analytical equipment) (not part of my invention). Overall, the apparatus is indicated by reference numeral 100.

Specifically referring to FIG. 1B, pressurized gas (e.g., air) from, for example, a pressurized air vessel 11, is passed through line 12 into the apparatus of my invention, initially through line 17 via entry port 40. In FIG. 1B, pressure indicator 13 is located on line 12, and pressure indicator 27 is located in the outer enclosure means 18 whereby a pressure drop between line 14 primarily across porous wall 20 is measured.

Referring specifically to FIG. 1C, carrier gas from gas source 10 is pulled through the apparatus by means of vacuum pump means 23 located downstream from the trapping means 22. Inert carrier gas is pulled through the apparatus using vacuum pump means 23 through line 28 which is connected to trapping means 22. The resulting trapped components may then be conveyed (on the trapping substance via conveying means 30) to analysis means 24 (which analysis means is not part of my invention).

Referring specifically to FIG. 1D, the central section of inner enclosure means 19 is composed of glass frit shown by reference numeral 42. Carrier gas entering at entry port 40 into void 34 within the inner enclosure means then passes through the glass frit 42 and through the pliable porous substrate 20. The passage of the inert gas again is shown by reference numeral 26 wherein the carrier gas now containing molecules of volatile substance is passed into void 25 of outer enclosure means 18.

Referring to FIG. 1E, inner support means 42a (Ronningen-Petter Woven Synthetic Screen) supports the pliable porous substrate containing volatile composition therein and/or thereon 20.

Referring to FIG. 2, inert carrier gas, e.g., air, passes through tube 17 past apparatus entry location 50 through entry port 40 (the entry port for the inner enclosure means) into void 34 and then through fritted glass 42 into the void between the outer container means 18 and the inner container means 19. The flow of carrier gas is shown by reference numeral 26. The top of the outer enclosure means is sealed to the lower section thereof 18 (which has base 18a) with TEFLON®, (Registered Trademark of E. I. Du Pont de Nemours and Company, Wilmington, Del., U.S.A.) seal 49. The carrier gas containing molecules of volatile substance is then passed through line 21 past SWAGELOK®, (Registered Trademark of the Swagelok Co. of Solon, Ohio, U.S.A.) connector 48 into TENAX® trap 22. The fritted glass support 42, in the case of the apparatus of FIG. 2, is 4" in length×1.5" in diameter and will hold a piece of cloth 4" in length×5.25" in width.

Referring to FIG. 3A, the apparatus 100 contains the upper inlet tube 18 and an inner enclosure means 42 having base 36 and outer enclosure means 18 having base 18a. Carrier gas flows through tube 21 into TENAX® trap or SPME trap 22.

Referring to FIG. 3B, the pliable porous substrate 20 is a section of a towel which is to be juxtaposed immediately adjacent to and fully covering the fritted glass central part of the inner enclosure means 42.

Referring to FIG. 3C, the void space of the inner enclosure means 34 has carrier gas flowing therethrough in a direction perpendicular to the support means 42 for the pliable porous substrate 20 containing volatile composition (e.g., perfume composition) to be analyzed with the carrier gas flow being shown by reference numeral 26.

Figure 5:
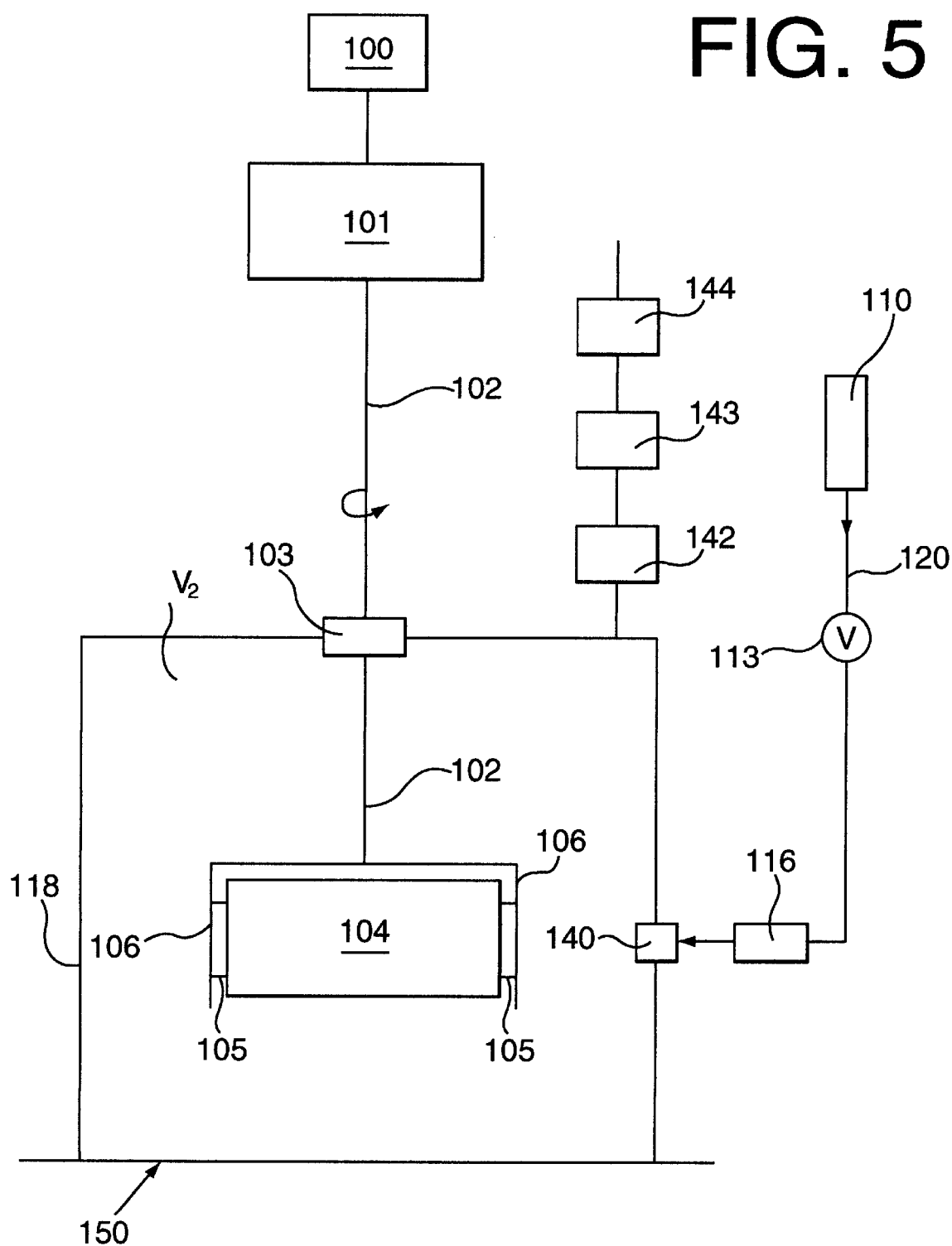
FIG. 5 is a block schematic block flow diagram showing the operation of the apparatus and the process of my invention, wherein the porous pliable substrate is rotated about a shaft.

Referring to FIG. 5, a variable speed control means 100 is provided to a motor means 101 which is connected to the upper part of a shaft 102 and sealing means 103. The sealing means is any suitable mechanical seal or packing which renders the hollow enclosure means substantially air tight, meaning that the contents of the hollow enclosure means will not leak into the ambient air, but rather will pass through the trap means 142 and the analysis means 143. The shaft means is connected at its lower end with the framing retaining means 106 and the attachment means 105 which maintains the porous, pliable substrate 104 in place. Pins, clips, wire, tape, hook and loop fasteners as well as other fasteners can be employed to attach the substrate to the framing retaining means. The framing retaining means is preferably a wire or metal device larger than the substrate use to hold the substrate in place while it is being rotated.

The inert gas source 110 is provided through a line 128 preferably through a valve 113, also preferably through a filter 116, into the hollow enclosure means 118 through the inlet means. The carrier gas is preferably directed against the rotating porous substrate in a head-on or direct manner. This will remove more of the volatile organic components from the porous substrate. The carrier gas and the volatile organic material will then flow via the pressure differential through the trap 142 and the analysis means 143 as discussed hereinabove. Vacuum means 144 is preferably provided to create a low pressure area further enabling the movement of the carrier gas and volatile organic materials into the trap and analysis means (wherein the volatile components thereof are collected for subsequent analysis). The hollow enclosure means is supported by an enclosure supporting means 150 such as table top, floor, lab bench or other suitable means to provide a substantially air tight seal between the hollow enclosure means and the enclosure supporting means.

FIG. 5 is a preferred embodiment of the invention in that the carrier gas is directed against the porous substrate and the trapping means is substantially perpendicular to the initial flow of the carrier gas. Substantially perpendicular is understood to mean that the angle between the inlet means and the trap is between about 70 and about 110 degrees; preferably about 90 degrees.

The detailed description of the operation of the apparatus of FIG. 3A is set forth in the description of Example I, infra.

Thus, the following examples are illustrative of my invention, but my invention is only limited by the scope of the claims following said examples.

EXAMPLE 1

Analysis of Contents of Fragrance Composition Releasably Adhered to Towel

Objective

To analyze the contents of a fragrance material originally situated in the interstices of a cotton towel.

Procedure

A 4"×5.25" cotton towel section containing 0.005% by weight fragrance composition is tightly wrapped around the central section of the inner enclosure of the apparatus of FIG. 3A. The inner enclosure thereof is composed of a porous fritted glass. Air from location 11 (FIG. 1B) is passed through the apparatus at a rate of 40 ml per minute for a period of 7 hours. Trapping means 22 contains a TENAX®-GC trap. At the end of the 7-hour period, the air flow was terminated and the TENAX®-GC trap was opened and the contents analyzed. The contents of the trap were analyzed by GC-MS analysis using a 50 m×0.32 mm OV-2 fused silica column having conditions: 80–220° C. at 8° C. per minute.

FIG. 4 is the GC mass spectrum for the perfume composition located on the towel, which is the subject of this example.

EXAMPLE 2

A towel having the dimensions of approximately 4 inches by approximately 5 inches, containing 0.005 weight percent fragrance is attached to the structure described in FIG. 5. Two trials were conducted, one trial was conducted were the towel remained stationary. In the second trial, the shaft was rotated at an speed of 82 revolutions per minute. In both trials the inert gas was provided to the enclosure means at a volume of 0.5 liters per minute. A chromatographic analysis of the headspace of the enclosure means was conducted.

FIG. 6A indicates the peaks found when the chromatographic analysis is performed while the towel was held stationary. FIG. 6B is the chromatographic analysis while the towel was rotated. As is evident from the chromatographic in FIG. 6B, the amount of material detected as much larger. In addition, there was a slight shifting of some of the peaks.

EXAMPLE 3

Two different commercially available fragrances were applied to a towel having the dimensions of Example 2 at a level of 0.005 weight percent. Using the apparatus described in FIG. 5, both fragrances were tested via while stationary and when rotated at a speed of 82 revolutions per minute. In all tests, the inert gas carrier was supplied to the hollow enclosure means at a rate of about 0.5 liters per minute.

Figure 7:
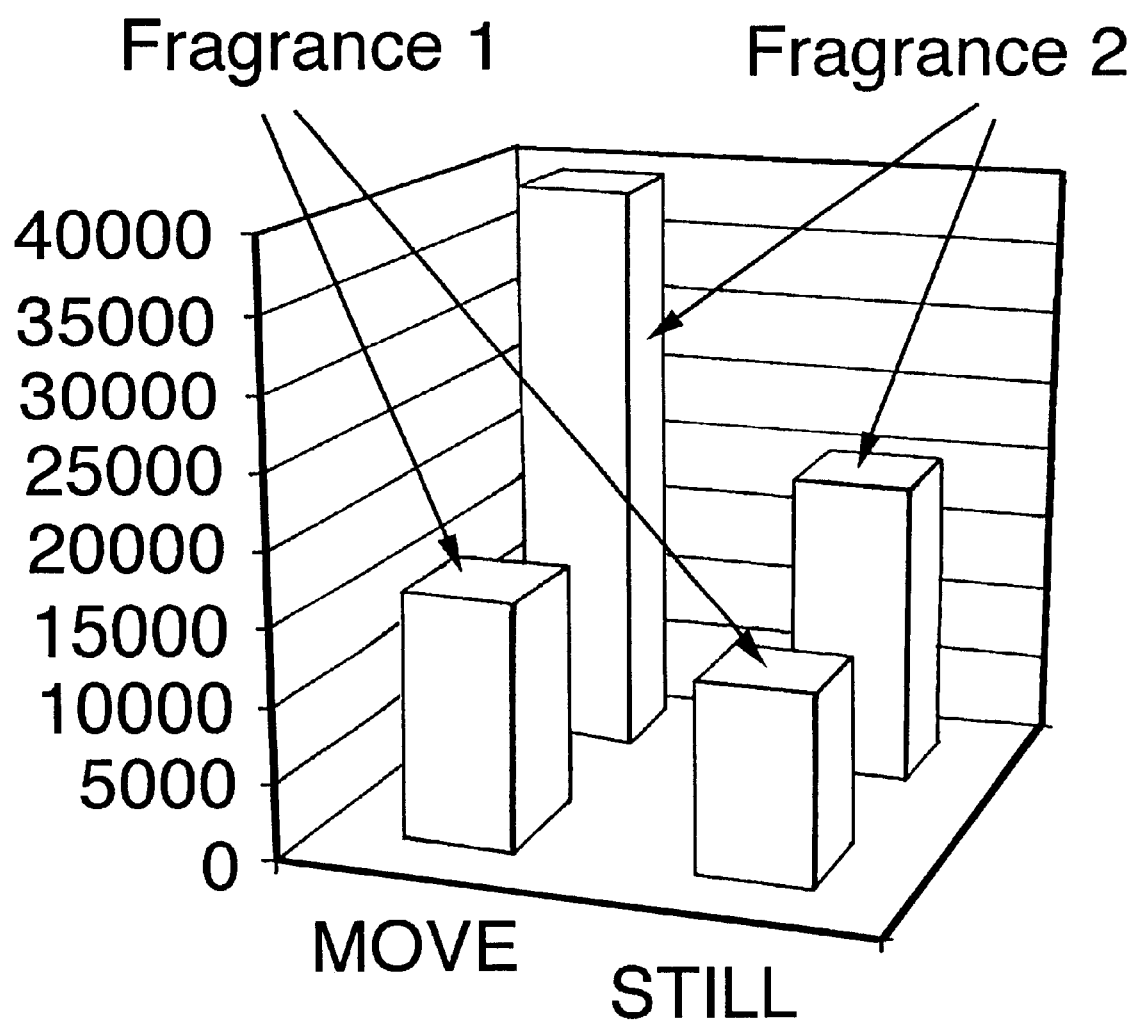
FIG. 7 is the graphical representation of the amount of fragrance detected by the apparatus of the present invention as tested at rest and also while in motion.

FIG. 7 demonstrates the increase in volatile compounds detected from both fragrances when rotated compared to the stationary test.

What is claimed is:

1. A process for carrying out collection of analyte, for the purpose of effecting qualitative and quantitative analysis of a volatile analyte composition releasably bonded to a substantially pliable porous substrate having an inner vertically-positioned surface and an outer vertically-positioned surface, said substrate being porous to the passage of a carrier gas and being fixedly retained by a rigid framing retaining means, as a vertically positioned substantially planar lamina, consisting essentially of the steps of:

(a) providing apparatus consisting essentially of:
  i. vertically-positioned rotational shaft means having an upper end section, a middle section, a lower end section, and a vertically-disposed shaft means axis;
  ii. vertically-positioned framing retaining means connected to said lower end section of said rotational shaft means;
  iii. hollow substantially air-tight enclosure means surrounding a void space, supported on a horizontally-disposed supporting means, and having a horizontally-disposed lid, a vertically-positioned cylindrical wall circumventing and extending upwardly from said horizontally-disposed supporting means and downwardly from the circumference of said horizontally-disposed lid, a vertical enclosure means axis, carrier gas exit port means therethrough, carrier gas first entry port means therethrough, gas-impermeable second entry port means therethrough located at the intersection of said vertical enclosure means axis and said lid for sealably holding in place said rotational shaft means at its middle section with the vertically-disposed shaft means axis of said rotational shaft means being coincident with said vertical enclosure means axis and sealably extending through said second entry port means into said void space and with said vertically-positioned framing retaining means being supported by and attached to said rotational shaft means located at the lower end section of said rotational shaft means, for retaining said pliable porous substrate;
  iv. attachment means for attaching said pliable porous substrate to said framing retaining means;
  v. rotational motor means attached to the upper end section of said rotational shaft means for causing said rotational shaft means to rotate about said vertically-disposed shaft means axis when said apparatus is in operation;
  vi. analyte collection means located downstream from said hollow enclosure means and communicating with said exit port means thereof, consisting essentially of tube trapping means whereby analyte mixture components emitted from said pliable porous substrate during gas flow therethrough are entrapped in said tube trapping means; and
  vii. upstream from said hollow enclosure means or downstream from said analyte collection means, gas flow effecting means for effecting the flow of gas sequentially (I) from a location upstream from said first entry port means; (II) through said first entry port means; (III) into said hollow enclosure means in a direction substantially perpendicular to the plane of said porous substrate located on and attached to said framing retaining means; (IV) onto the inner surface of said porous substrate; (V) through said porous substrate, exiting from said outer surface thereof; (VI) through said exit port means of said hollow enclosure means and (VII) into and through said analyte collection means;

(b) providing said porous substrate and attaching said porous substrate via said attachment means to said framing retaining means;

(c) engaging said rotational motor means;

(d) simultaneously with the engagement of said rotational motor means, upstream from said hollow enclosure means or downstream from said analyte collection means effecting the flow of carrier gas sequentially (I) from a location upstream from said first entry port means; (II) through said first entry port means; (III) into said hollow enclosure means in a direction substantially perpendicular to the plane of said porous substrate located on and attached to said framing retaining means; (IV) onto the inner surface of said porous substrate; (V) through said porous substrate, exiting from said outer surface thereof; (VI) through said exit port means of said hollow enclosure means and (VII) into and through said analyte collection means whereby volatile substance components emitted from said porous substrate are trapped in said analyte collection means.

2. The process of claim 1 wherein the flow of carrier gas is effected upstream from said hollow enclosure means by means of pressurizing the carrier gas upstream from said hollow enclosure means.

3. The process of claim 1 wherein the flow of carrier gas is effected downstream from said analyte collection means using vacuum pump means located downstream from said analyte collection means.

4. The process of claim 1 wherein the volatile substance molecules are emitted substantially perpendicular to the direction of the carrier gas as it enters the hollow enclosure means.

5. The process of claim 1 wherein the rotational motor means is operated in the range of from about 10 up to about 150 revolutions per minute.

6. The process of claim 5 wherein the rotational motor means is operated in the range of from about 50 up to about 90 revolutions per minute.

7. The process of claim 6 wherein the rotational motor means is operated at about 82 revolutions per minute.

8. The process of claim 1 wherein the carrier gas is an inert gas and the gas flow rate of the carrier gas is in the range of from about 0.1 up to about 1 liter per minute.

9. The process of claim 8 wherein flow rate of the carrier gas is in the range of from about 0.3 up to about 0.7 liter per minute.

10. The process of claim 9 wherein the flow rate of the carrier gas is about 0.5 liter per minute.

11. The process of claim 5 wherein flow rate of the carrier gas is in the range of from about 0.1 up to about 1 liter per minute.

12. The process of claim 11 wherein the flow rate of the carrier gas is in the range of from about 0.3 up to about 0.7 liter per minute.

13. The process of claim 12 wherein the flow rate of the carrier gas is about 0.5 liter per minute.

14. The process of claim 1 wherein the flow rate of carrier gas is in the range of from about 20 ml. per minute up to about 200 ml. per minute.

* * * * *